(12) United States Patent
Rauber

(10) Patent No.: US 8,564,656 B2
(45) Date of Patent: Oct. 22, 2013

(54) METHOD FOR IDENTIFYING SURFACE CHARACTERISTICS OF METALLURGICAL PRODUCTS, ESPECIALLY CONTINUOUSLY CAST AND ROLLED PRODUCTS, AND A DEVICE FOR CARRYING OUT SAID METHOD

(75) Inventor: Tobias Rauber, Kusnacht (CH)

(73) Assignee: SMS Concast AG, Zurich (CH)

( * ) Notice: Subject to any disclaimer, the term of this patent is extended or adjusted under 35 U.S.C. 154(b) by 960 days.

(21) Appl. No.: 12/531,340

(22) PCT Filed: Mar. 19, 2008

(86) PCT No.: PCT/EP2008/002206
§ 371 (c)(1),
(2), (4) Date: Sep. 15, 2009

(87) PCT Pub. No.: WO2008/113579
PCT Pub. Date: Sep. 25, 2008

(65) Prior Publication Data
US 2010/0103256 A1    Apr. 29, 2010

(30) Foreign Application Priority Data
Mar. 19, 2007    (EP) .................................... 07405087

(51) Int. Cl.
*G06K 9/00*    (2006.01)
*C07F 7/04*    (2006.01)
*G06F 19/00*    (2011.01)
*G06Q 10/00*    (2012.01)

(52) U.S. Cl.
USPC ............. 348/92; 382/106; 382/142; 382/154; 556/430; 700/180; 700/182; 705/301

(58) Field of Classification Search
None
See application file for complete search history.

(56) References Cited

U.S. PATENT DOCUMENTS

| | | | | |
|---|---|---|---|---|
| 4,809,342 A | * | 2/1989 | Kappner | 382/142 |
| 4,847,778 A | * | 7/1989 | Daley | 700/180 |
| 5,444,388 A | * | 8/1995 | Ideta et al. | 324/750.25 |
| 5,471,307 A | * | 11/1995 | Koliopoulos et al. | 356/613 |
| 5,715,166 A | * | 2/1998 | Besl et al. | 700/182 |
| 6,184,924 B1 | * | 2/2001 | Schneider et al. | 348/92 |
| 6,222,628 B1 | * | 4/2001 | Corallo et al. | 356/601 |
| 6,327,374 B1 | * | 12/2001 | Piironen et al. | 382/108 |
| 2002/0083856 A1 | * | 7/2002 | Hutchison et al. | 101/368 |
| 2002/0116980 A1 | * | 8/2002 | Kerr et al. | 73/1.14 |
| 2003/0151008 A1 | * | 8/2003 | Yamada | 250/559.45 |
| 2004/0189944 A1 | * | 9/2004 | Kaufman et al. | 352/10 |
| 2004/0246473 A1 | * | 12/2004 | Hermary et al. | 356/237.1 |
| 2005/0219537 A1 | * | 10/2005 | Tange et al. | 356/430 |

(Continued)

*Primary Examiner* — Ario Etienne
*Assistant Examiner* — Ho Shiu
(74) *Attorney, Agent, or Firm* — Brian Roffe

(57) ABSTRACT

The invention relates to a method for recognizing surface characteristics of metallurgical products, especially continuously cast products and rolled products. According to said method, a defined section of the product surface (12, 12') is irradiated by at least two radiation sources of different wavelengths, from different directions, and the irradiated surface section is optoelectronically detected. Three light sources (21, 22, 23) are oriented towards the product surface (12, 12'), as radiation sources, under the same angle (a), the positions thereof being in three planes (E1, E2, E3) forming a 120 DEG angle and being perpendicular to the product surface (12, 12'). In this way, instructive information about metallurgical products can be determined and stored in a very short space of time such that the products can be determined in a perfectly identified manner for the reprocessing, in terms of the surface quality or surface structure thereof.

20 Claims, 3 Drawing Sheets

(56) References Cited

U.S. PATENT DOCUMENTS

| | | | |
|---|---|---|---|
| 2005/0264307 A1* | 12/2005 | Setaka | 324/754 |
| 2006/0041448 A1* | 2/2006 | Patterson et al. | 705/1 |
| 2006/0254679 A1* | 11/2006 | Odashima et al. | 148/551 |
| 2008/0013826 A1* | 1/2008 | Hillis et al. | 382/154 |
| 2009/0091738 A1* | 4/2009 | Morcom | 356/5.03 |

* cited by examiner

METHOD FOR IDENTIFYING SURFACE CHARACTERISTICS OF METALLURGICAL PRODUCTS, ESPECIALLY CONTINUOUSLY CAST AND ROLLED PRODUCTS, AND A DEVICE FOR CARRYING OUT SAID METHOD

The invention relates to a device for identifying metallurgical products, especially for continuously cast and rolled products, and to a device for carrying out said method.

Metallurgical products, especially continuously cast and rolled products such as blooms, slabs or billets, blanks, sheets, strips etc. are tracked and registered in the production flow and between further processing stages. For this purpose, specific surface characteristics, such as for example specifically applied marks or also other quality-relevant characteristics, such as for example surface defects, are observed and assigned to the respective product.

For the marking, sometimes marking machines with a marking stamp and an impact apparatus are normally used, as is known for example from WO 03/074295.

In a method and apparatus for identifying objects according to publication WO 00/37926 an object to be identified is illuminated by means of at least two light sources from different directions and angles, and here a camera records this object and the shadows produced by the light sources from a pre-specified position. With this method and apparatus any deviations of the external form of the object are to be recorded. This type of method is not suitable and is not provided for recording surface characteristics.

The object, which forms the basis of the present invention, is to propose a method and to provide a device which make it possible to reliably establish and to store instructive information about surface characteristics of metallurgical products, especially continuously cast and rolled products, under production conditions.

This object is achieved according to the invention by a method and a device with the characteristics of Claim 1 and Claim 4.

Further preferred embodiments of the method and the device according to the invention form the subject matter of the dependent claims.

The method according to the invention makes it possible to establish and to store a huge amount of instructive information about metallurgical products in an extremely short space of time such that the latter can be correctly identified for further processing.

In the following the invention is described in greater detail by means of the drawings. The latter show, purely diagrammatically:

Figure 1:
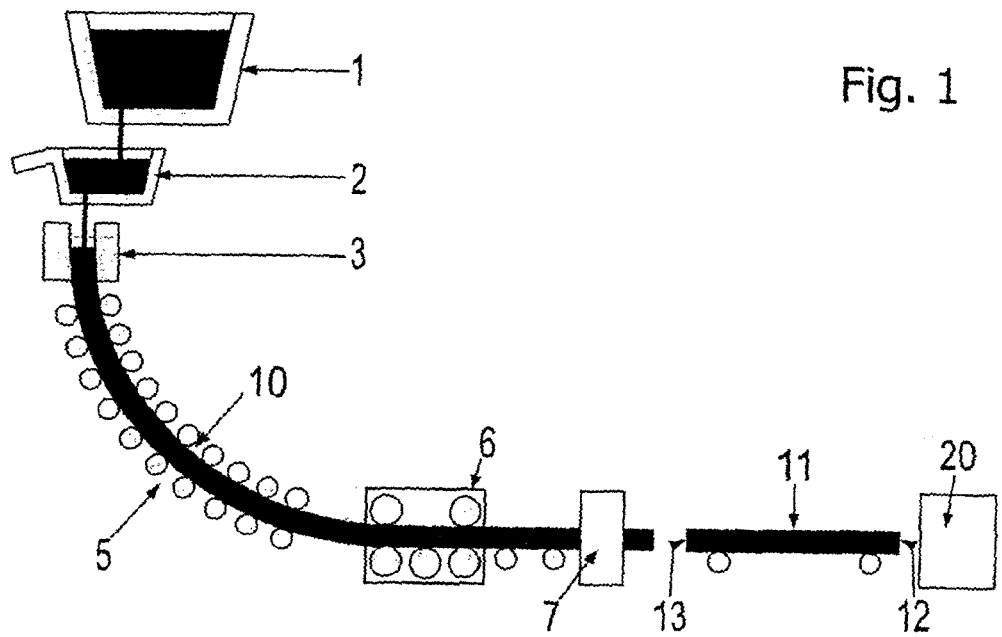
FIG. 1 is the structure, in principle, of a continuous casting installation.

FIG. 1 diagrammatically shows the structure, in principle, of a continuous casting installation, known in its own right, comprising a casting ladle 1, a intermediate receptacle 2 (tundish), a casting die 3 cooled with water and a bar deflection device 5 for the bar 10. In the example shown of a so-called bending installation the hot bar 10 is bent under the drawing component 5 by rolling in the horizontal and is pressed by rollers 6. After this the bar 10 is separated into pieces 11 in a separation component 7 (e.g. burner or cutter)—depending on the casting cross-section of the casting die 3—said pieces being blooms, slabs or billets which are then further processed in the roller mill to form blanks, sheets, strips etc.

In order to identify or recognize the pieces or semi-products 11, which are for example conveyed away in a direction perpendicular to the drawing plane of FIG. 1, one of the two separation surfaces 12, 13 produced by separating the bar 10, according to FIG. 1 the product surface 12, is optically recorded for recognition by means of a device 20 according to the invention, as will now be described in the following by means of FIGS. 2 to 4.

Figure 2:
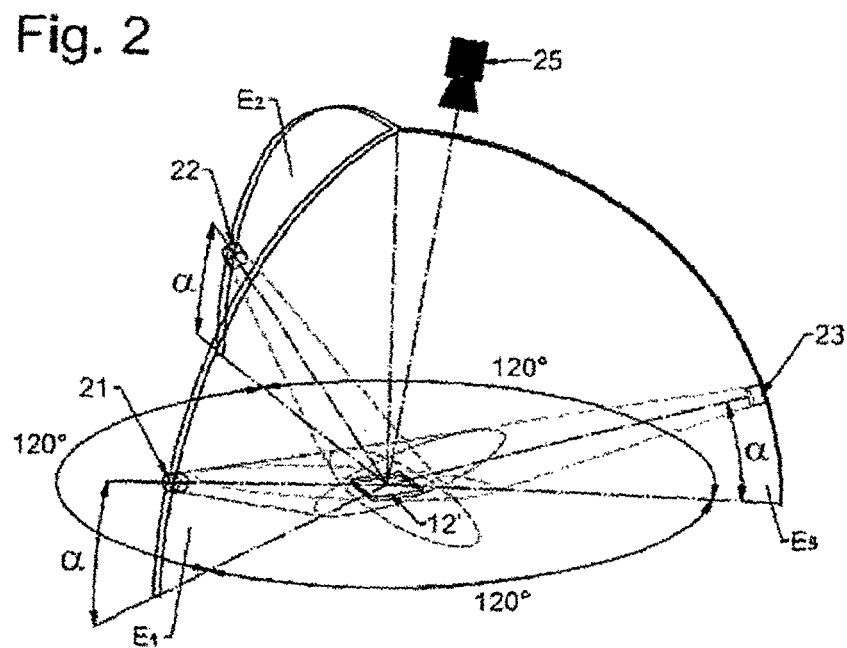
FIG. 2 is a first exemplary embodiment of a device according to the invention for recording a product surface.

With the embodiment diagrammatically illustrated in FIG. 2, according to the method of the invention a product surface 12' (for example the aforementioned separation surface 12 of a bloom) is illuminated by three light sources 21, 22, 23 disposed at different locations. All three light sources 21, 22, 23, the locations of which lie in three planes $E_1$, $E_2$, $E_3$ together enclosing an angle of 120° and perpendicular to the product surface 12, are oriented at the same angle $\alpha$ towards the product surface 12. An image sensor, preferably a digital camera 25, is provided with which the illuminated product surface 12 is recorded in a selected section with corresponding shadows and reflections. The images and dot matrices obtained in this way contain, in addition to the information for the recognition of the product, an enormous amount of information on the surface properties and the surface structure, e.g. about surface defects, cracks, slag inclusions, scratches, etc.

Figure 4:
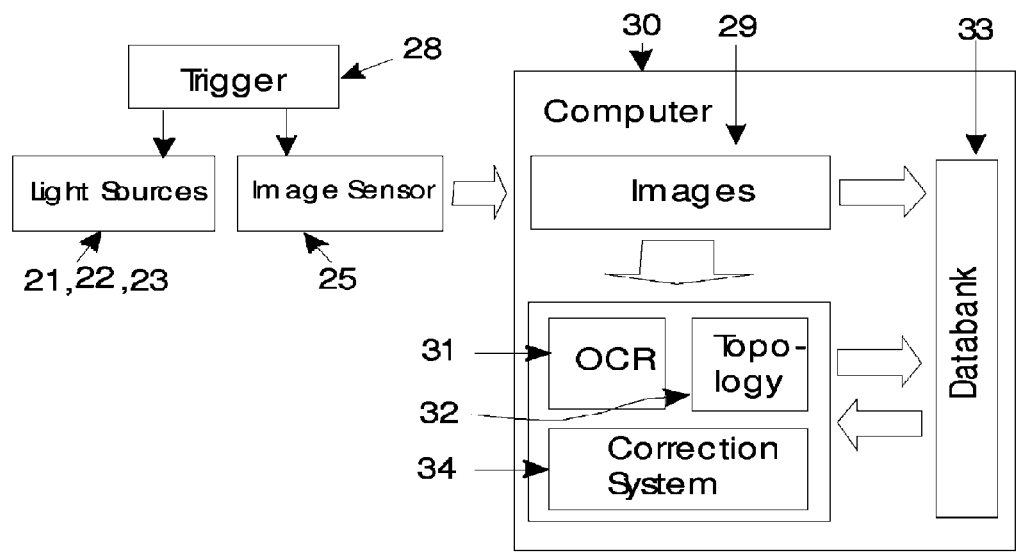
FIG. 4 is a block diagram of a device according to the invention for identifying metallurgical products, in particular continuously cast products.

As indicated in the block diagram according to FIG. 4, the images 29 obtained after triggering 28 the illumination and the camera are recorded in a computer 30 and stored in a databank 33 from where they can be retrieved at any time for recognition.

LEDs (light emitting diodes), which have a substantially longer life and greater efficiency in comparison, for example, with halogen lamps, are preferably used as light sources 21, 22, 23.

When using different color LEDs (and a digital color camera 25) advantageous results are achieved. Particularly suitable is the use of the light colors red, green and blue.

When simply using different color LEDs, OCR (optical character recognition) 31 is suitable as the recording and recognition system.

When using RGB (Red/Green/Blue) LEDs, both OCR 31 and three-dimensional topology (fingerprint) 32 are suitable as a recording and recognition system.

For both identification and recognition systems a defect identification and correction system 34 is provided.

The device 20 according to the invention enables sharp recording of moving parts, e.g. of the continuously cast products. The best contrast is achieved with a relatively small angle $\alpha$ (approx. 10°-20°).

The information about the three-dimensional topology can be improved by stereo technology, i.e. by using two cameras. Two cameras can also contribute to the improvement of contrast.

Figure 3:
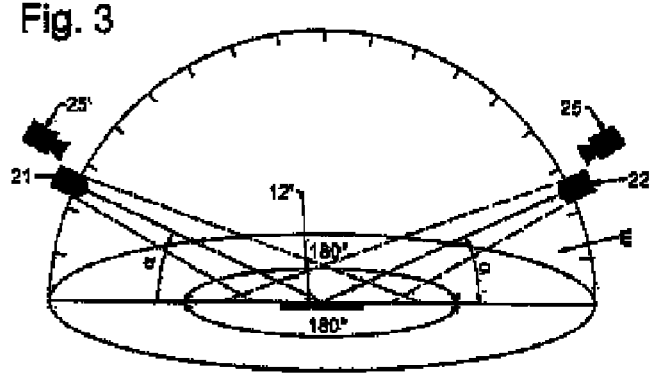
FIG. 3 is a second exemplary embodiment of a device according to the invention for recording a product surface.

As shown by FIG. 3, it is also possible to use just two colors of LED 21, 22, for example with the light colors red and green, and to accept incomplete information about the three-dimensional topology. With this embodiment the locations of the light emitting diodes 21, 22 come in a common plane E perpendicular to the product surface 12'. Here too, instead of a single camera, two cameras 25, 25' can be used, the primary reason for this being improved contrast with larger angles α, and not the production of a stereo photograph.

The device according to the invention makes it possible to establish and to store a huge amount of instructive information about metallurgical products, in particular continuously cast products, in an extremely short space of time, such that the latter can be correctly identified for further processing.

Figure 5A:
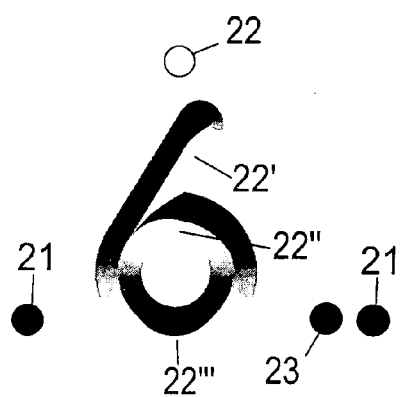
FIGS. 5a to 5c are respective diagrammatic illustrations of a mark illuminated by respective light sources (number 6).
Figure 5B:
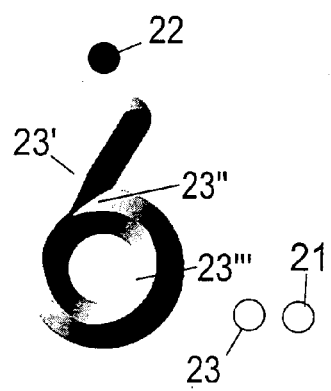
Figure 5C:
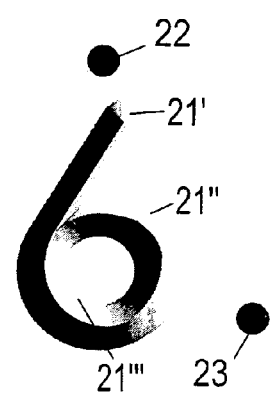

FIGS. 5a to 5b show an exemplary embodiment according to the invention of a mark made in the product surface; this is illustrated, as an example, by a stamped number 6. In turn, three light sources 21, 22, 23 are disposed oriented towards a centre at an angle of 120°. These three light sources respectively produce a color and shade image, as is illustrated in these figures. As viewed in the cross-section, this number 6 forms a V shape, and so with the bright light source 22 on the top side correspondingly bright illumination is produced on the illuminated surfaces of this number 6 at points 22', 22", 22'". In FIG. 5b the light source 23 is switched on which produces corresponding illumination at points 23', 23", 23'", and in FIG. 5c the light source 21 produces corresponding illumination at points 21', 21", 21'". This mark is applied here to this section before the optoelectronic recording.

Between this mark, for example the stamped number or similar, and the light sources radiating onto this number from different directions and the color and shade image thus produced, an interaction is achieved which enables particularly reliable optoelectronic identification. Therefore, these marks are advantageously very specifically formed, and this provides particularly strong contrast and safeguards them against confusion. These can be classic numbers or letters, but also specially formed characters which correspond to these desired requirements.

One thus gains the substantial advantage that by placing simple marks in the section of the product surface intended for identification and recognition, many different identification characteristics can be produced.

In theory, 2 light sources are sufficient. Advantageously however, 3 are used. However, even more than three could be used. Invisible rays, such as infrared or similar, could also be used as radiation sources.

The device can also be designed such that it is portable and therefore can be installed mobilely and temporarily at any desired location.

The invention claimed is:

1. A method for identifying surface characteristics of elongate metallurgical pieces formed from separation of a bar into the pieces, comprising:
    applying a mark to at least one separation surface at an end of one of the pieces, each separation surface being one of the surfaces that faces a surface of an adjacent piece formed from the same bar; and
    deriving information about the surface characteristics of the piece based on analysis of interaction between the mark and radiation,
    the information deriving step comprising:
        directing radiation of a first wavelength from a first radiation source at a portion of the at least one separation surface including the mark to cause interaction between the mark and the directed radiation;
        directing radiation of a second wavelength from a second radiation source at a portion of the at least one separation surface including the mark to cause interaction between the mark and the directed radiation, the second wavelength being different than the first wavelength;
        directing radiation of a third wavelength from a third radiation source at a portion of the at least one separation surface including the mark to cause interaction between the mark and the directed radiation, the third wavelength being different than the first and second wavelengths, the first, second and third radiation sources being positioned relative to one another such that the mark on the at least one separation surface is irradiated by the first, second and third radiation sources from three different directions;
    obtaining at least one image of a portion of the at least one separation surface including the mark, using at least one digital imaging device, while the mark has radiation from the first, second and third radiation sources directed thereto;
    storing the at least one image in a data storage device; and
    enabling analysis of the at least one image to identify surface characteristics of the piece including at least one of an identification of the piece, surface properties of the piece, and surface structure of the piece.

2. The method of claim 1, wherein the first, second and third radiation sources are configured to direct visible light at the at least one separation surface.

3. The method of claim 1, wherein the at least one digital imaging device comprises a digital camera.

4. The method of claim 1, further comprising:
    retrieving the at least one image from the data storage device; and then
    analyzing the retrieved at least one image to identify the surface characteristics of the piece.

5. The method of claim 1, further comprising directing the obtained at least one image to an analysis system and analyzing the at least one image using the analysis system to identify the surface characteristics of the piece.

6. The method of claim 1, wherein the step of applying the mark to the at least one separation surface comprises including in the mark, information about the surface structure of the piece including information about at least one of surface defects, cracks, slag inclusions, and scratches.

7. The method of claim 1, further comprising orienting the first, second and third radiation sources at a common angle relative to the at least one separation surface.

8. The method of claim 7, further comprising positioning the first, second and third radiation sources apart from one another at an angle of 120°.

9. The method of claim 7, further comprising positioning each of the first, second and third radiation sources in a respective plane to be perpendicular to the at least one separation surface, wherein the planes are separated from one another by an angle of 120°.

10. The method of claim 1, further comprising positioning the first, second and third radiation sources apart from one another at an angle of 120°.

11. The method of claim 1, further comprising positioning each of the first, second and third radiation sources in a respective plane to be perpendicular to the at least one separation surface, wherein the planes are separated from one another by an angle of 120°.

12. The method of claim 1, wherein the at least one digital imaging device consists of a single digital color camera.

13. The method of claim 1, wherein the first radiation source is configured to direct red light, the second radiation source is configured to direct green light, and the third radiation source is configured to direct blue light.

14. The method of claim 1, wherein the first, second and third radiation sources each comprise at least one light emitting diode.

15. The method of claim 1, further comprising analyzing the at least one image using an analysis system to identify the surface characteristics of the piece, the analysis system being configured to use at least one three-dimensional topology (finger print) and OCR (optical character recognition) to derive information about the piece from the applied mark.

16. The method of claim 1, further comprising analyzing the at least one image and a dot matrix corresponding to each of the at least one image using an analysis system to identify the surface characteristics of the piece.

17. An arrangement for identifying surface characteristics of elongate metallurgical pieces formed upon separation of a bar, the arrangement comprising:
   a system for deriving information about the surface characteristics of the piece based on analysis of interaction between a mark and radiation, wherein the mark is on at least one separation surface at an end of each of the pieces, the separation surface being one of the surfaces that faces a surface of an adjacent piece formed from the same bar, said system comprising:
   a first radiation source that directs radiation of a first wavelength at a portion of the at least one separation surface including the mark to cause interaction between the mark and the directed radiation;
   a second radiation source that directs radiation of a second wavelength at a portion of the at least one separation surface including the mark to cause interaction between the mark and the directed radiation, the second wavelength being different than the first wavelength;
   a third radiation source that directs radiation of a third wavelength at a portion of the at least one separation surface including the mark to cause interaction between the mark and the directed radiation, the third wavelength being different than the first and second wavelengths, said first, second and third radiation sources being positioned relative to one another such that the mark on the at least one separation surface is irradiated by said first, second and third radiation sources from three different directions;
   at least one digital imaging device that obtains at least one image of the mark on the at least one separation surface while the mark on the at least one separation surface is being radiated by said first, second and third radiation sources;
   a data storage device that stores the at least one image; and
   an analysis system that enables analysis of the at least one image to identify surface characteristics of the piece including at least one of an identification of the piece, surface properties of the piece, and surface structure of the piece.

18. The arrangement of claim 17, wherein each of said first, second and third radiation sources is positioned in a respective plane, wherein the planes are separated from one another by an angle of 120°.

19. The arrangement of claim 17, wherein said first radiation source is configured to direct red light, said second radiation source is configured to direct green light, and said third radiation source is configured to direct blue light.

20. The arrangement of claim 17, wherein said analysis system is configured to use at least one of three-dimensional topology (finger print) and OCR (optical character recognition) to derive information about the piece from the applied mark.

* * * * *